(12) United States Patent
Liu et al.

(10) Patent No.: US 10,139,360 B2
(45) Date of Patent: Nov. 27, 2018

(54) AUTOMATIC CODING DEVICE, BIOSENSOR WITH SAME AND MANUFACTURING METHOD THEREFOR

(71) Applicant: LEADWAY (HK) LIMITED, Hong Kong (CN)

(72) Inventors: Tao Liu, Zhejiang (CN); Huanxi Ge, Zhejiang (CN); Chia-Lin Wang, San Diego, CA (US); Yun Ye, Zhejiang (CN)

(73) Assignee: LEADWAY (HK) LIMITED, Hong Kong (CN)

( * ) Notice: Subject to any disclaimer, the term of this patent is extended or adjusted under 35 U.S.C. 154(b) by 376 days.

(21) Appl. No.: 14/389,698

(22) PCT Filed: Jan. 30, 2013

(86) PCT No.: PCT/CN2013/071119
§ 371 (c)(1),
(2) Date: Sep. 30, 2014

(87) PCT Pub. No.: WO2013/143357
PCT Pub. Date: Oct. 3, 2013

(65) Prior Publication Data
US 2015/0047977 A1  Feb. 19, 2015

(30) Foreign Application Priority Data

Mar. 31, 2012 (CN) .......................... 2012 1 0095099
Jan. 30, 2013 (WO) ................ PCT/CN2013/071119

(51) Int. Cl.
*G01N 27/327* (2006.01)
*G01N 33/487* (2006.01)
(Continued)

(52) U.S. Cl.
CPC ..... *G01N 27/327* (2013.01); *G01N 33/48771* (2013.01); *G01N 35/00693* (2013.01);
(Continued)

(58) Field of Classification Search
CPC ....... G01N 33/48771; G01N 35/00693; G01N 27/327; G01N 2035/00811;
(Continued)

(56) References Cited

U.S. PATENT DOCUMENTS 512,420 A    1/1894  Willits
4,714,874 A  12/1987  Morris et al.
(Continued)

FOREIGN PATENT DOCUMENTS

CN    101156066 A    4/2008
CN    101874204 A    10/2010
(Continued)

OTHER PUBLICATIONS

The Extended European Search Report issued in EP 13768748 dated Jan. 20, 2016.
(Continued)

*Primary Examiner* — Tamir Ayad
(74) *Attorney, Agent, or Firm* — Acuity Law Group, PC; Michael A. Whittaker

(57) ABSTRACT

The present invention provides an automatic encoding device including a first electrode, a second electrode, and a third electrode. The first electrode and the second electrode are connected through a connecting point, so that an electric parameter between the first electrode and the second electrode changes according to a parameter needing to be corrected. The present invention further provides a method for applying the automatic encoding device to various biosensors and a method for manufacturing the automatic encoding device. Positions and the number of contacts for
(Continued)

connecting the automatic encoding device and a detection system are fixed. Therefore, connection sites on the detection system are effectively utilized. On the other hand, the automatic encoding device in the present invention can provide different parameter information by only changing the positions of the connecting points on the electrodes, the process is simple and stable, and the probability of human errors is reduced.

5 Claims, 7 Drawing Sheets

(51) Int. Cl.
*H05K 3/02* (2006.01)
*G01N 35/00* (2006.01)

(52) U.S. Cl.
CPC ... *H05K 3/027* (2013.01); *G01N 2035/00782* (2013.01); *G01N 2035/00811* (2013.01); *Y10T 29/49155* (2015.01); *Y10T 29/49156* (2015.01)

(58) Field of Classification Search
CPC .......... G01N 2035/00782; H05K 3/027; Y10T 29/49155; Y10T 29/49156
USPC ............................... 204/403.01; 29/846, 847
See application file for complete search history.

(56) References Cited

U.S. PATENT DOCUMENTS

| | | |
|---|---|---|
| 5,141,868 A | 8/1992 | Shanks et al. |
| 5,320,732 A | 6/1994 | Nankai et al. |
| 5,366,609 A | 11/1994 | White et al. |
| 7,418,285 B2 | 8/2008 | Ghesquiere et al. |
| 2005/0279647 A1* | 12/2005 | Beaty ..................... B01L 3/545 205/792 |
| 2009/0014327 A1 | 1/2009 | Ghesquiere et al. |
| 2009/0095622 A1 | 4/2009 | Cho et al. |
| 2009/0095623 A1 | 4/2009 | Boiteau et al. |
| 2010/0170791 A1 | 7/2010 | Lee |
| 2010/0294660 A1 | 11/2010 | Wang et al. |

FOREIGN PATENT DOCUMENTS

| | | |
|---|---|---|
| CN | 102967636 A | 3/2013 |
| CN | 202794094 U | 3/2013 |
| EP | 1256798 A1 | 11/2002 |
| EP | 1431758 A1 | 6/2004 |
| WO | 2008076212 A1 | 6/2008 |
| WO | 2009014890 A1 | 1/2009 |
| WO | 2013017218 A1 | 2/2013 |

OTHER PUBLICATIONS

The International Search Report issued in PCT/CN2013/071119 dated May 2, 2013.

* cited by examiner

AUTOMATIC CODING DEVICE, BIOSENSOR WITH SAME AND MANUFACTURING METHOD THEREFOR

The present invention is filed under 35 U.S.C. § 371 as the U.S. national phase of International Application No. PCT/CN2013/071119, filed Jan. 30, 2013, which designated the U.S. and claims the benefit of priority to Chinese Patent Application No. 201210095099.9 filed Mar. 31, 2012, each of which is hereby incorporated in their entirety including all tables, figures, and claims.

FIELD OF THE INVENTION

The present invention relates to an automatic encoding device, a biosensor with the automatic encoding device, and a manufacturing method for manufacturing the automatic encoding device.

DESCRIPTION OF THE RELATED ART

In recent years, from original detection using clinical laboratory samples to rapid detection which can be accomplished in a doctor's office or right beside a patient, medical healthcare has changed significantly. Disposable enzymology biosensors are often used in rapid detection. By using the catalysis function of enzyme specificity, various biosensors are developed, for example, a biosensor for blood glucose measurement. An electrochemical method of the biosensor is generally as follows: an anode and a cathode are fixed on an insulating substrate, and the electrodes are covered with a reaction reagent. After a sample is added, a target substance in the sample is subjected to an oxidation reduction reaction under the catalysis of enzyme, oxygen or an electron transfer carrier is reduced, and at the moment, the reduced oxygen or electron transfer carrier is compulsively oxidized and releases electrons due to the electrode potential, causing a change of electrons. A method of quantifying such electron change to indirectly detect the content of the target substance is an electrochemical detection method, for example, U.S. Pat. Nos. 5,120,420, 5,320,732, and 5,141,868 all disclose disposable biosensors for measuring blood glucoses. These sensors each consist of two plastic pieces which are laminated together. A sample can be introduced into an internal reaction area through ventilation capillary channels formed in such a structure. The sample is contacted with an enzyme layer and electrodes on the biosensor and is reacted, and a detection instrument collects reaction signals transmitted from the biosensor, and detects an analyte in the sample.

With the technical development, various types of detection using biosensors can be accomplished with only one detection instrument. Therefore, to ensure that the detection is performed correctly, the detection instrument should determine the type of detection performed by the currently used biosensor. In addition, in the production process, biosensors in different batches are different in certain degree, and the detection instrument should judge differences among different batches of biosensors.

The U.S. Pat. No. 5,366,609 adopts a pluggable memory key. First, correction information such as detection type information or information about a difference between batches is stored in the memory key; when being used, the key is inserted into the detection instrument, and after reading the information in the key, the detection instrument correspondingly corrects a signal transmitted from the biosensor, and finally gives a detection result. Each memory key corresponds to only one batch of biosensors. Therefore, when using a memory key, a user needs to determine whether a batch number of the currently used biosensor corresponds to a batch number of the corresponding memory key. Such design in which the correction information is separated from the biosensor has the following defects: first, the user needs to perform two steps of operation when using a biosensor for detection, that is, inserting the memory key and inserting the biosensor, which is very inconvenient in use; and secondly, as a memory key needs to be manually inserted in advance, it is possible that the user forgets to perform this step.

In view of the foregoing defects, the U.S. Pat. No. 7,415,285 discloses integrating correction information into a biosensor, so as to accomplish functions of correction and detection in one step of operation. The biosensor includes a working electrode, a reference electrode, and a comparison electrode for correcting a difference between batches. Resistances of the electrodes are adjusted through different thicknesses or patterns of the electrodes, and different resistances correspond to different parameters. However, the thicknesses and the patterns of the electrodes may deviate in the production process, and it is hard to obtain uniform resistance absolute values of the electrodes. This causes correction information of different biosensors of one same batch to be different, and the detection result is not accurate.

The US patent US20100170791A1 discloses a biosensor, which includes an electrode for recording parameter information of the biosensor. The electrode comprises an electrode pattern and multiple contacts formed on the electrode pattern according to the parameter information, and the parameter information is a resistance ratio of the multiple contacts. The US patent overcomes the defect that electrodes with uniform resistances are hard to obtain in the production process. However, the biosensor still has the following defects: when a great deal of correction information needs to be stored, a biosensor needs multiple contacts to accomplish the judgment task, correspondingly, the number of connecting points on the detection instrument needs to be increased, and thus the detection instrument is insufficient in compatibility. When the number of connecting points of the detection instrument is less than that of contacts of the biosensors, the detection instrument cannot work normally. When the number of connecting points of the detection instrument is more than that of contacts of the biosensors, redundant connecting points are left unused, which not only occupy space but also increase the cost of the product.

SUMMARY OF THE INVENTION

To overcome the above-mentioned defects, the present invention provides an automatic encoding device, a biosensor with the automatic encoding device, and a manufacturing method for the automatic encoding device.

Technical solution 1: an automatic encoding device, including an insulating base plate and an electrode system positioned on the insulating base plate, where the electrode system includes a first electrode (11), a second electrode (12), and a third electrode (13); the first electrode (11), the second electrode (12), and the third electrode (13) respectively include a first contact (21), a second contact (22), and a third contact (23) which are electrically connected with a detection instrument; the first electrode (11) and the second electrode (12) are selectively electrically connected with a first connecting point (31); the second electrode (12) and the third electrode (13) are selectively electrically connected with a second connecting point (32); a loop formed by the first contact (21), the first connecting point (31), and a second contact (22) corresponds to an electric parameter R1; a loop formed by the second contact (22), the second connecting point (32), and the third contact (23) corresponds to an electric parameter R2; a loop formed by the first contact (21), the first connecting point (31), the second connecting point (32), and the third contact (23) corresponds to an electric parameter R3; and subsequently, a group of codes are obtained according to one of the following formulas:

$$S1 = K1 * \frac{R1}{R2},$$

or $$S2 = K2 * \frac{R3}{R2},$$

or $$S3 = K3 * \frac{R1}{R3}$$

where K1, K2 and K3 are correction coefficients, respectively.

Technical solution 2: the automatic encoding device according to technical solution 1, where least the second electrode includes a zigzag snake-shaped structure.

Technical solution 3: the automatic encoding device according to technical solution 2, where at least the second electrode includes a plurality of snake-shaped units, and electric parameters of the snake-shaped units are substantially the same.

Technical solution 4: the automatic encoding device according to technical solution 3, where corresponding codes are determined according to the number of snake-shaped units included in the loop formed by the first contact (21), the first connecting point (31), and the second contact (22) and the number of snake-shaped units included in the loop formed by the first contact (21), the first connecting point (31), the second connecting point (32), and the third contact (23).

Technical solution 5: the automatic encoding device according to technical solution 1, further including a fourth electrode (14), where the fourth electrode (14) is electrically connected with the second electrode through a third connecting point (33), and each different position of the third connecting point (33) corresponds to one group of codes.

Technical solution 6: a biosensor, including an insulating base plate, and a working electrode (41) and a counter electrode (42) that are positioned on the insulating base plate, at least one of the working electrode (41) and the counter electrode (42) being provided with a reaction reagent layer, the biosensor further including an automatic encoding device, where the automatic encoding device includes an electrode system positioned on the insulating base plate; the electrode system includes a first electrode (11), a second electrode (12), and a third electrode (13); the first electrode (11), the second electrode (12), and the third electrode (13) respectively include a first contact (21), a second contact (22), and a third contact (23) which are electrically connected with a detection instrument; the first electrode (11) and the second electrode (12) are selectively electrically connected with a first connecting point (31); the second electrode (12) and the third electrode (13) are selectively electrically connected with a second connecting point (32); a loop formed by the first contact (21), the first connecting point (31), and the second contact (22) corresponds to an electric parameter R1; a loop formed by the second contact (22), the second connecting point (32), and the third contact (23) corresponds to an electric parameter R2; a loop formed by the first contact (21), the first connecting point (31), the second connecting point (32), and the third contact (23) corresponds to an electric parameter R3; and subsequently, a group of codes are obtained according to one of the following formulas:

$$S1 = K1 * \frac{R1}{R2},$$

or $$S2 = K2 * \frac{R3}{R2},$$

or $$S3 = K3 * \frac{R1}{R3}$$

where K1, K2, and K3 are correction coefficients, respectively.

Technical solution 7: the biosensor according to technical solution 6, where at least the second electrode includes a zigzag snake-shaped structure, the second electrode includes a plurality of snake-shaped units, and electric parameters of the snake-shaped units are substantially the same.

Technical solution 8: the biosensor according to technical solution 7, where corresponding codes are determined according to the number of snake-shaped units included in the loop formed by the first contact (21), the first connecting point (31), and the second contact (22) and the number of snake-shaped units included in the loop formed by the first contact (21), the first connecting point (31), the second connecting point (32), and the third contact (23).

Technical solution 9: the biosensor according to technical solution 6, further including a fourth electrode (14), where the fourth electrode (14) is electrically connected with the second electrode through a third connecting point (33), and each different position of the third connecting point (33) corresponds to one group of codes.

Technical solution 10: the biosensor according to any one of technical solutions 6 to 9, where the automatic encoding device is positioned on the same surface of the insulating base plate as the working electrode and the counter electrode or on an opposite surface of the insulating base plate relative to the working electrode and the counter electrode.

Technical solution 11: the biosensor according to technical solution 6, where that the first electrode (11) and the second electrode (12) are selectively electrically connected with the first connecting point (31) refers to that the encoding device corresponds to different codes when the first connecting point (31) for connecting the first electrode (11) and the second electrode (12) is at different positions, and likewise, that the second electrode (12) and the third electrode (13) are selectively electrically connected with the second connecting point (32) refers to that the encoding device corresponds to different codes when the second connecting point (32) for connecting the second electrode (12) and the third electrode (13) is at different positions.

Technical solution 12: an automatic encoding device, including an insulating base plate and an electrode system positioned on the insulating base plate, where the electrode system includes a first electrode (11), a second electrode (12), and a third electrode (13); the first electrode (11), the second electrode (12), and the third electrode (13) respectively include a first contact (21), a second contact (22), and a third contact (23) which are electrically connected with a detection instrument; at least the second electrode (12) includes a zigzag snake-shaped structure; the first electrode (11) and the second electrode (12) are selectively electrically connected with a first connecting point (31); the second electrode (12) and the third electrode (13) are selectively electrically connected with a second connecting point (32); when the first connecting point (31) is at a first position, a loop formed by the first contact (21), the first connecting point (31), and the second contact (22) corresponds to an electric parameter R1; when the first connecting point (31) is at a second position, a loop formed by the first contact (21), the first connecting point (31), and the second contact (22) corresponds to an electric parameter R1'; and values of the electric parameters R1 and R1' correspond to two groups of different codes, respectively.

Technical solution 13: the automatic encoding device according to technical solution 12, where a loop formed by the second contact (22), the second connecting point (32), and the third contact (23) corresponds to an electric parameter R2; a loop formed by the first contact (21), the first connecting point (31), the second connecting point (32), and the third contact (23) corresponds to an electric parameter R3; the electric parameters R1, R2, and R3 correspond to a first group of codes, and the electric parameters R1', R2, and R3 correspond to a second group of codes.

Technical solution 14: the automatic encoding device according to technical solution 13, where one group of codes are obtained according to one of the following formulas:

$$S1 = K1 * \frac{R1}{R2},$$

or $$S2 = K2 * \frac{R3}{R2},$$

or $$S3 = K3 * \frac{R1}{R3}$$

where K1, K2 and K3 are correction coefficients, respectively, and another group of codes are obtained when R1 is replaced by R1'.

Technical solution 15: a biosensor, including an insulating base plate, and a working electrode (41) and a counter electrode (42) that are positioned on the insulating base plate, at least one of the working electrode (41) and the counter electrode (42) being provided with a reaction reagent layer, the biosensor further including an automatic encoding device, where the automatic encoding device includes an electrode system positioned on the insulating base plate; the electrode system includes a first electrode (11), a second electrode (12), and a third electrode (13); the first electrode (11), the second electrode (12), and the third electrode (13) respectively include a first contact (21), a second contact (22), and a third contact (23) which are electrically connected with a detection instrument; at least the second electrode includes a zigzag snake-shaped structure; the first electrode (11) and the second electrode (12) are selectively electrically connected with a first connecting point (31); the second electrode (12) and the third electrode (13) are selectively electrically connected with a second connecting point (32); when the first connecting point (31) is at a first position, a loop formed by the first contact (21), the first connecting point (31), and the second contact (22) corresponds to an electric parameter R1; when the first connecting point (31) is at a second position, a loop formed by the first contact (21), the first connecting point (31), and the second contact (22) corresponds to an electric parameter R1'; and values of the electric parameters R1 and R1' correspond to two groups of different codes, respectively.

Technical solution 16: the biosensor according to technical solution 15, where a loop formed by the second contact (22), the second connecting point (32), and the third contact (23) corresponds to an electric parameter R2; a loop formed by the first contact (21), the first connecting point (31), the second connecting point (32), and the third contact (23) corresponds to an electric parameter R3; the electric parameters R1, R2, and R3 correspond to a first group of codes; and the electric parameters R1', R2, and R3 correspond to a second group of codes.

Technical solution 17: the biosensor according to technical solution 16, where one group of codes are obtained according to one of the following formulas:

$$S1 = K1 * \frac{R1}{R2},$$

or $$S2 = K2 * \frac{R3}{R2},$$

or $$S3 = K3 * \frac{R1}{R3}$$

where K1, K2, and K3 are correction coefficients, respectively, and another group of codes are obtained when R1 is replaced by R1'.

Technical solution 18: a manufacturing method for an automatic encoding device, including the following steps:
providing an insulating base plate, where at least an electrode system including a first electrode (11), a second electrode (12), and a third electrode (13) is positioned on the insulating base plate;
connecting the first electrode with the second electrode through a first connecting point (31);
connecting the second electrode with the third electrode through a second connecting point (32); and
determining a connection position of the first connecting point (31) between the first electrode and the second electrode according to information to be encoded by the automatic encoding device.

Technical solution 19: the manufacturing method according to technical solution 18, where a connection position of the second connecting point (32) between the second electrode and the third electrode is determined according to the information to be encoded by the automatic encoding device.

Technical solution 20: the manufacturing method according to technical solution 18, where conducting materials are disposed at positions corresponding to the first connecting point and the second connecting point by means of printing.

Technical solution 21: the manufacturing method according to technical solution 18, where first, multiple connection sites are formed between the first electrode and the second electrode by means of printing, and subsequently other connection sites except the first connecting point between the first electrode and the second electrode are cut off by means of laser cutting.

Technical solution 22: the manufacturing method according to technical solution 18, where first, multiple connection sites are formed between the second electrode and the third electrode by means of printing, and subsequently other connection sites except the second connecting point between the second electrode and the third electrode are cut off by means of laser cutting.

Technical solution 23: the manufacturing method according to technical solution 18, where the second electrode (12) is composed of snake-shaped units.

Technical solution 24: the manufacturing method according to technical solution 18, where the insulating base plate is further provided with a fourth electrode (14), and the fourth electrode (14) is connected with the second electrode (12) through a third connecting point (33).

The present invention has the following beneficial effects: according to different production batches of biosensors, different correction equations such as temperature correction equation and hematocrit (HCT) correction equation, or different types of analytes, a connecting point is disposed at different positions between two electrodes, so that the resistance of the loop between the two electrodes is different according to different positions of the connecting point, and electric parameters provided by the automatic encoding device are also different. The detection instrument selects correction parameters of the biosensor according to the different electric parameters of the automatic encoding device, and finally a detection result is obtained or the type of analyte detection performed is determined. According to the present invention, positions of contacts between the automatic encoding device and the detection instrument do not need to be changed, and positions and the number of contacts, in contact with the detection instrument, on the automatic encoding device are fixed. Therefore, connection sites on the detection instrument are effectively utilized, space of the detection instrument is saved, and the product cost is effectively controlled. On the other hand, the automatic encoding device in the present invention can provide different parameters by only changing the positions of the connecting points on the electrodes. Such change is much easier than changing an electrode pattern. Moreover, a template for manufacturing the electrode system can remain unchanged, the manufacturing process is simple and stable, and the probability of human errors is reduced.

Figure 1:
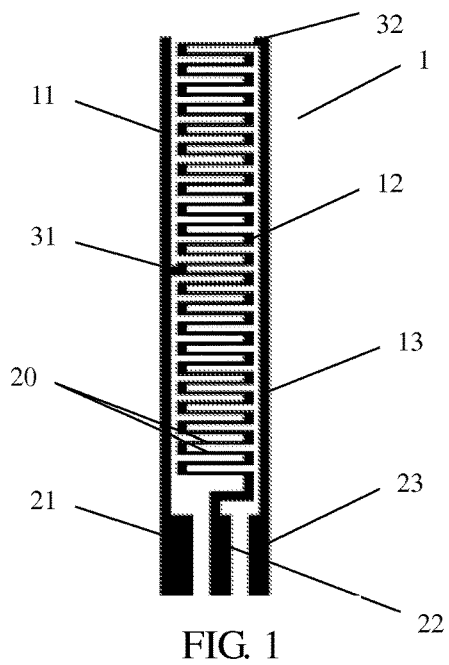
FIG. 1 is a schematic diagram of an automatic encoding device with three electrodes.

Reference numerals: automatic encoding device 1; first electrode 11; second electrode 12; third electrode 13; fourth electrode 14; resistor unit 20; first connecting point 31; second connecting point 32; third connecting point 33; working electrode 41; counter electrode 42; insulating layer 51, 215; notch 61; contact 21, 22, 23, 24, 25, 26, 231, 232, 233, 234; biosensor 100; biosensor electrode system 103, 105, 107; insulating base plate 210; cover layer 225; gap layer 220; vent hole 226; reaction reagent layer 310.

DETAILED DESCRIPTION OF THE INVENTION

The present invention is described in detail as follows with reference to the drawings. These embodiments are merely finite enumerations without departing from the spirit of the present invention, and other specific implementation solutions produced when persons skilled in the art combine the prior art with the present invention are not excluded.

Figure 2:
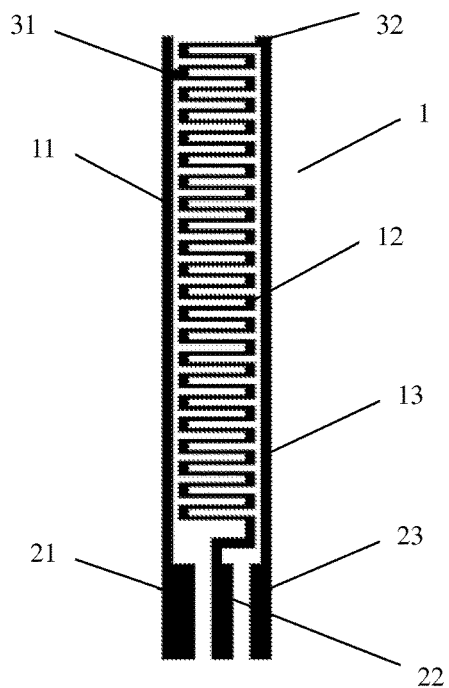
FIG. 2 is a schematic diagram of an automatic encoding device on which positions of connecting points are different from those shown in FIG. 1.

As shown in FIG. 1 and FIG. 2, an electrode group of an automatic encoding device 1 according to the present invention includes a first electrode 11, a second electrode 12, and a third electrode 13. The first electrode, the second electrode, and the third electrode are connected with a detection instrument through a first contact 21, a second contact 22, and a third contact 23 on pins of the electrodes. The electrode 11 is selectively electrically connected with the electrode 12 through a connecting point 31. After the first contact 21 and the second contact 22 are contacted with the detection instrument, a loop is formed between the electrode 11 and the electrode 12. That the electrode 11 is selectively electrically connected with the electrode 12 through the connecting point 31 refers to that for different automatic encoding devices with different codes, the structures are substantially the same, but positions of the first connecting point 31 are different. Therefore, a resistance of a loop formed by the first contact 21, the first connecting point 31, and the second contact 22 changes according to different positions of the first connecting point 31 on the electrodes, thereby corresponding to different codes. For this reason, a connection position of the first connecting point 31 between the first electrode and the second electrode can be determined according to information needing to be encoded by the automatic encoding device. The position of the connecting point 31 in FIG. 1 is closer to the pin of the electrode than the connecting point in FIG. 2, and therefore, the route of the loop between the electrode 11 and the electrode 12 in FIG. 1 is shorter than the route of the loop in FIG. 2. As shown in FIG. 1, when the first connecting point 31 is at the first position, the loop formed by the first contact 21, the first connecting point 31, and the second contact 22 corresponds to an electric parameter R1. As shown in FIG. 2, when the first connecting point 31 is at the second position, the loop formed by the first contact 21, the first connecting point 31, and the second contact 22 corresponds to an electric parameter R1'. When materials and patterns of the electrodes 11, 12, and 13 in FIG. 1 and FIG. 2 are the same, because of the different positions of the connecting point, the resistance R1 of the loop between the electrode 11 and the electrode 12 in FIG. 1 is smaller than the resistance R1' of the loop between the electrode 11 and the electrode 12 in FIG. 2. Likewise, the resistance of the loop between the electrode 11 and the electrode 13 in FIG. 1 is greater than the resistance of the loop between the electrode 11 and the electrode 13 in FIG. 2. In the embodiments shown in FIG. 1 and FIG. 2, the position of the second connecting point 32 between the electrode 12 and the electrode 13 is fixed. Therefore, the resistance of the loop between the electrode 12 and the electrode 13 in FIG. 1 and FIG. 2 is fixed. In another implementation manner, as the position of the second connecting point 32 between the electrode 12 and the electrode 13 can change like the first connecting point 31, more codes can be obtained. The electrodes can be designed into various shapes, and the electrode 12 shown in the figures is of a zigzag snake-shaped structure and is composed of a plurality of snake-shaped units 20. The electrode 12 and the electrode 13 are connected at an end far away from the second contact 22 and the third contact 23, and the electrode 11 is connected with the electrode 12 through the first connecting point 31.

After the automatic encoding device shown in FIG. 1 or FIG. 2 is electrically connected with the detection instrument through the contacts, encoding of information is realized using one of the following methods.

Method One:

After the automatic encoding device is electrically connected with the detection instrument through the contacts, the detection instrument measures that the resistance of the loop 1 between the electrode 11 and the electrode 12 is R1, and the resistance of the loop 2 between the electrode 12 and the electrode 13 is R2. A resistance ratio S1 of the loop 1 to the loop 2 is obtained through equation 1.

$$S1 = K1 * \frac{R1}{R2} \quad (1)$$

where K1 is a correction coefficient.

According to different production batches of biosensors, different parameter correction equations such as temperature correction equation and, HCT correction equation, or different measured analytes, the connecting point 31 is disposed at different positions between the electrode 11 and the electrode 12, so that the resistance R1 of the loop between the electrode 11 and the electrode 12 is different according to different demands. Therefore, the resistance ratio S1 provided by the automatic encoding device is also different. The detection instrument can select corresponding technical parameters according to different values of S1, to finally obtain a detection result or determine the type of analyte detection performed.

Method Two:

After the automatic encoding device is electrically connected with the detection instrument through the contacts, the detection instrument measures that the resistance of the loop 3 between the electrode 11 and the electrode 13 is R3, and the resistance of the loop 2 between the electrode 12 and the electrode 13 is R2. A resistance ratio S2 of the loop 3 to the loop 2 is obtained through equation 2.

$$S2 = K2 * \frac{R3}{R2} \quad (2)$$

where K2 is a correction coefficient.

According to different production batches of biosensors, different parameter correction equations such as temperature correction equation and HCT correction equation, or different measured analytes, the connecting point 31 is disposed at different positions between the electrode 11 and the electrode 12, so that the resistance R3 of the loop between the electrode 11 and the electrode 13 is different according to different demands. Therefore, the resistance ratio S2 provided by the automatic encoding device is also different. The detection instrument selects corresponding technical parameters according to different values of S2, to finally obtain a detection result or determine the type of analyte detection performed.

Method Three:

After the automatic encoding device is electrically connected with the detection instrument through the contacts, the detection instrument measures that the resistance of the loop 1 between the electrode 11 and the electrode 12 is R1, the resistance of the loop 3 between the electrode 11 and the electrode 13 is R3, and a resistance ratio S3 of the loop 1 to the loop 3 is obtained through equation 3.

$$S3 = K3 * \frac{R1}{R3} \quad (3)$$

where K3 is a correction coefficient.

According to different production batches of biosensors, different parameter correction equations such as temperature correction equation and HCT correction equation, or different measured analytes, the connecting point 31 is disposed at different positions between the electrode 11 and the electrode 12, so that the resistance R1 of the loop between the electrode 11 and the electrode 12 is different, and the resistance R3 of the loop between the electrode 11 and the electrode 13 is different. Therefore, the resistance ratio S3 provided by the automatic encoding device is also different. The detection instrument selects corresponding technical parameters according to different values of S3, to finally obtain a detection result or determine the type of analyte detection performed.

Figure 3:
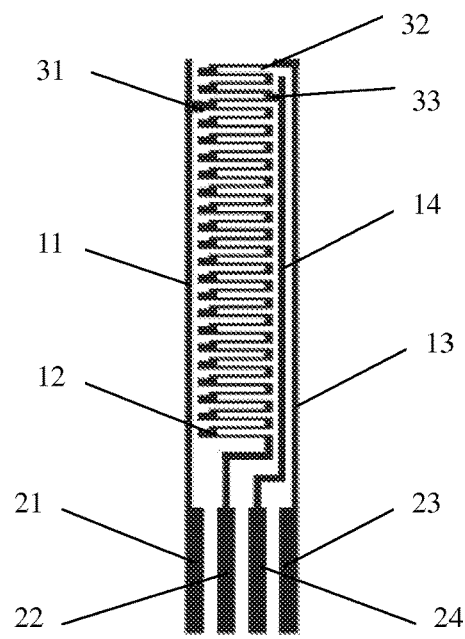
FIG. 3 is a schematic diagram of an automatic encoding device with four electrodes.
Figure 4:
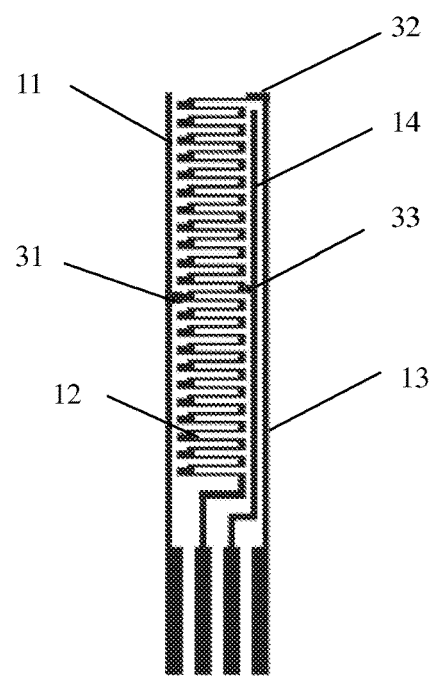
FIG. 4 is a schematic diagram of an automatic encoding device on which positions of connecting points are different from those shown in FIG. 3.
Figure 5:
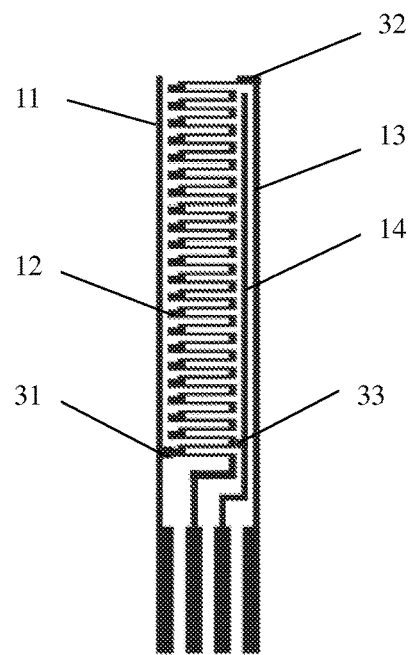
FIG. 5 is a schematic diagram of an automatic encoding device on which positions of connecting points are different from those shown in FIG. 3 and FIG. 4.

The automatic encoding device disclosed by the present invention is not limited to including only the foregoing three electrodes but may further include more electrodes. As shown in FIG. 3 to FIG. 5, the automatic encoding device includes a first electrode 11, a second electrode 12, a third electrode 13, and a fourth electrode 14. The first electrode, the second electrode, the third electrode, and the fourth electrode are connected with a detection instrument through contacts 21, 22, 23, and 24 on the electrodes. The electrode 11 is electrically connected with the electrode 12 through a connecting point 31, the resistance R1 of a loop between the electrode 11 and the electrode 12 is different according to different positions of the connecting point 31 on the electrodes, and the resistance R3 between the electrode 11 and the electrode 13 is different according to different positions of the connecting point 31 on the electrodes. The electrode 12 is connected with the electrode 13 at an end far away from the contacts 22 and 24 through a connecting point 32. The electrode 12 is electrically connected with the electrode 14 through a connecting point 33, the resistance R4 of a loop between the electrode 12 and the electrode 14 is different according to different positions of the connecting point 33 on the electrodes, and the resistance R5 of a loop between the electrode 13 and the electrode 14 is different according to different positions of the connecting point 33 on the electrodes.

After the automatic encoding devices shown in FIG. 3, FIG. 4, and FIG. 5 are electrically connected with the detection instrument through the contacts, encoding of information is realized using one of the following methods.

Method four:

After the automatic encoding devices shown in FIG. 3 to FIG. 5 are electrically connected with the detection instrument through the contacts, the detection instrument measures that the resistance of the loop 1 between the electrode 11 and the electrode 12 is R1, the resistance of the loop 2 between the electrode 12 and the electrode 13 is R2, and a resistance ratio S1 of the loop 1 to the loop 2 is calculated according to equation 1.

$$S1 = K1 * \frac{R1}{R2} \quad (1)$$

where K1 is a correction coefficient.

The resistance of a loop 4 between the electrode 12 and the electrode 14 is R4, and a resistance ratio S4 of the loop 4 to the loop 2 is calculated according to equation 4.

$$S4 = K4 * \frac{R4}{R2} \quad (4)$$

where K4 is a correction coefficient.

The detection instrument selects corresponding technical parameters according to information about different combinations of values of S1 and S4, to finally obtain a detection result or determine the type of analyte detection performed.

Method five:

After the automatic encoding devices shown in FIG. 3 to FIG. 5 are electrically connected with the detection instrument through the contacts, the detection instrument measures that the resistance of the loop 1 between the electrode 11 and the electrode 12 is R1, the resistance of the loop 2 between the electrode 12 and the electrode 13 is R2, and a resistance ratio S1 of the loop 1 to the loop 2 is calculated according to equation 1.

$$S1 = K1 * \frac{R1}{R2} \quad (1)$$

where K1 is a correction coefficient.

The resistance of the loop 5 between the electrode 13 and the electrode 14 is R5, and a resistance ratio S5 of the loop 5 to the loop 2 is calculated according to equation 5.

$$S5 = K5 * \frac{R5}{R2} \quad (5)$$

where K5 is a correction coefficient.

The detection instrument selects corresponding technical parameters according to information about different combinations of values of S1 and S5, to finally obtain a detection result or determine the type of analyte detection performed.

Method six:

After the automatic encoding devices shown in FIG. 3 to FIG. 5 are electrically connected with the detection instrument through the contacts, the detection instrument measures that the resistance of the loop 1 between the electrode 11 and the electrode 12 is R1, the resistance of the loop 3 between the electrode 12 and the electrode 13 is R3, and a resistance ratio S3 of the loop 1 to the loop 2 is calculated according to equation 3.

$$S3 = K3 * \frac{R1}{R3} \quad (3)$$

where K3 is a correction coefficient.

The resistance of the loop 4 between the electrode 12 and the electrode 14 is R4, the resistance of the loop 5 between the electrode 13 and the electrode 14 is R5, and a resistance ratio S6 of the loop 4 to the loop 5 is calculated according to equation 6.

$$S6 = K6 * \frac{R4}{R5} \quad (6)$$

where K6 is a correction coefficient.

The detection instrument selects corresponding technical information according to information about different combinations of values of S3 and S6, to finally obtain a detection result or determine the type of analyte detection performed.

After the automatic encoding devices in FIG. 3, FIG. 4, and FIG. 5 are electrically connected with the detection instrument through the contacts, modes for implementing information encoding are not limited to the above-mentioned methods but include other combined modes.

In the embodiments shown in FIG. 1 and FIG. 2, the electrode 12 is composed of n snake-shaped units 20 (for example, the value of n is 22). The resistances of the snake-shaped units are substantially the same, for example, the resistance is R', and the resistance of the loop between the electrode 12 and the electrode 13 is R''. The resistance ratio S between the two groups of electrodes can be obtained through the following equation:

$$S = k * \frac{x \cdot R'}{R''} = k * \frac{x \cdot R'}{n \cdot R'} = k \frac{x}{n}$$

where x represents the number of snake-shaped units in the loop between the first electrode and the second electrode; n represents the number of snake-shaped units in the loop between the second electrode and the third electrode; and k is a correction coefficient.

The equation shows that when x and n change, S changes correspondingly, thereby corresponding to different codes.

The detection instrument selects corresponding technical parameters according to different values of S, to perform corresponding detection data processing.

The value of S may be set to include a certain error range, for example, the error range is ±(1/2n), and within the range of S±(1/2n), the detection instrument chooses to use one same group of technical parameters for detection and result calculation.

The judgment by the detection instrument on the value of S may be different according to different positions of the connecting points. When the a connecting point is at either of two ends of the automatic encoding device, in the range of S±(1/2n), it is considered that one same group of technical parameters can be selected for detection and result calculation. When a connecting point is in the middle of the automatic encoding device, in the range of S±(1/n), it is considered that that one same group of technical parameters can be selected for detection.

More particularly, the electrode 12 shown in FIG. 1 and FIG. 2 is composed of 22 snake-shaped units. A sliding block 31 shown in FIG. 1 is in the middle of the automatic encoding device, and the loop between the electrode 11 and the electrode 12 includes 9.5 snake-shaped units. Therefore, S1 shown in FIG. 1 is (9.5/22). When the sliding block 31 shown in FIG. 2 is closer to the end part of the automatic encoding device, the loop between the electrode 11 and the electrode 12 includes 20.5 snake-shaped units, so S1 shown in FIG. 2 is (20.5/22). Therefore, the value of S1 measured by the automatic encoding device of FIG. 1 is different from the value of S1 measured by the automatic encoding device of FIG. 2, and the detection instrument selects corresponding technical parameters according to information about different values of S1, to finally obtain a detection result or determine the type of analyte detection performed.

Figure 6:
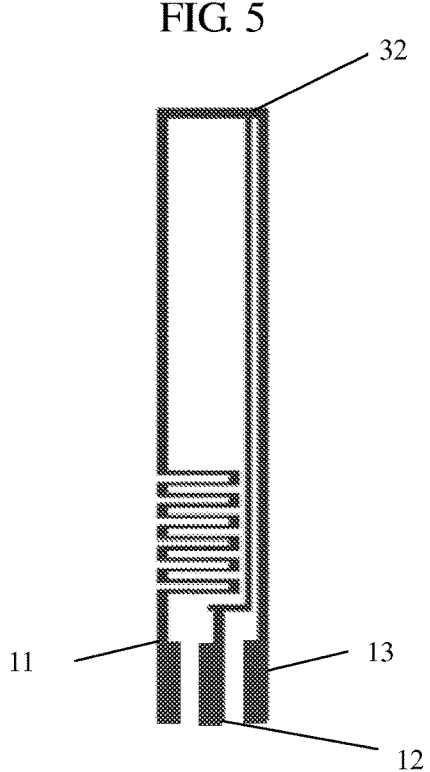
FIG. 6 is a schematic diagram of an automatic encoding device having a simple structure.
Figure 7:
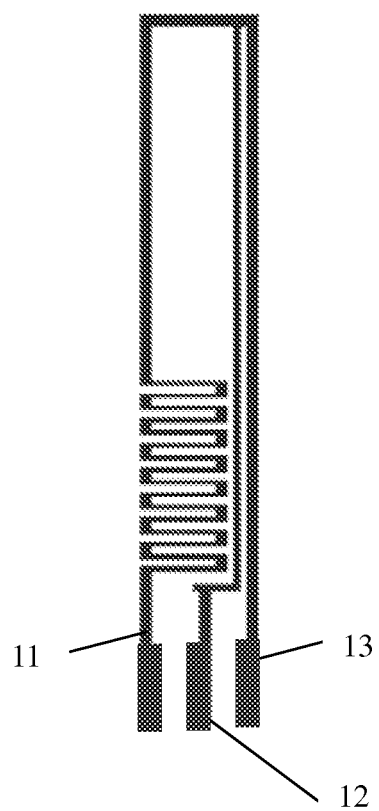
FIG. 7 is a schematic diagram of an automatic encoding device of which an electrode 11 has a resistance greater than that of an electrode 11 shown in FIG. 6.

According to the embodiments shown in FIG. 6 and FIG. 7, the resistance of the loop between the electrode 11 and the electrode 12 changes according to the resistance of the electrode 11. The total length of the conductive material of the electrode 11 in FIG. 6 is smaller than the total length of the conductive material of the electrode 11 in FIG. 7. Under the circumstance that the same conductive material is used, the resistance of the loop between the electrode 11 and the electrode 12 shown in FIG. 6 is smaller than the resistance between the electrode 11 and the electrode 12 shown in FIG. 11. According to the embodiments shown in FIG. 6 and FIG. 7, the resistance R2 of the loop between the electrode 12 and the electrode 13 is fixed. S1 can be obtained through calculation according to equation 1:

$$S1 = K1 * \frac{R1}{R2} \quad (1)$$

where K1 is a correction coefficient.

The detection instrument selects corresponding technical parameters according to different values of S1, to finally obtain a detection result or determine the type of analyte detection performed.

In other embodiments, the resistance of the loop between the electrode 12 and the electrode 13 may change according to different batches of products.

In the present invention, the first electrode 11 and the second electrode 12 are selectively connected with the first connecting point 31, that is, the connection position of the first connecting point 31 between the first electrode and the second electrode is determined according to information to be encoded by the automatic encoding device. The term "selectively" in the present invention refers to that the positions of the first connecting point 31, the second connecting point 32, and the third connecting point 33 can be selected according to electric parameters needed for encoding. In the present invention, the second electrode 12 and the third electrode 13 are selectively connected with the second connecting point 32, that is, the connection position of the second connecting point 32 between the second electrode and the third electrode is determined according to the information to be encoded by the automatic encoding device. In the present invention, the second electrode 12 and the fourth electrode 14 are selectively connected with the third connecting point 33, that is, the connection position of the third connecting point 33 between the second electrode and the fourth electrode is determined according to the information to be encoded by the automatic encoding device.

The number of electrodes of the automatic encoding device of the present invention may be three, four, or more. One, two, or more connecting points for connecting the electrodes may be provided. The pattern structures and calculation methods mentioned above do not constitute any limitation, but various methods designed according to the principle of the present invention are included.

The automatic encoding device of the present invention is applied to various biosensors such as an optical biosensor or an electrochemical biosensor, and is used for correcting a detection result or used for determining the type of analyte detection performed.

Figure 8:
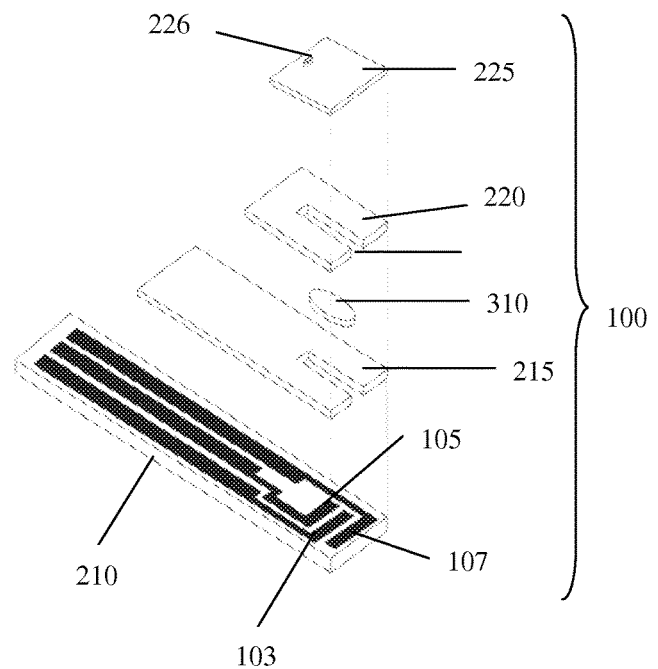
FIG. 8 is a schematic diagram of a biosensor for detecting an analyte in a sample.

In an embodiment shown in FIG. 8, a biosensor 100 includes an insulating base plate 210 with an electrode system (103, 105, 107), at least one reaction reagent layer 310 disposed on a working electrode 103, and a cover layer 225. The components of the device may be laminated together or adhered together using an adhesive, and may also be printed on the base plate to form the device. The electrode system on the insulating base plate at least includes the working electrode 103, a counter electrode 105, and a reference electrode 107. An insulating layer covers the electrode system, and an opening is provided in the front end of the insulating layer 215 above the electrode system. The reagent layer 310 is positioned inside the opening of the insulating layer 215 and covers the electrode system to form a reaction chamber.

The reaction reagent layer 310 is disposed on at least one electrode, and may also cover two or all electrodes. The reaction reagent layer contains one or more reagents for detecting whether a liquid sample contains the analyte or for detecting the content of the analyte.

In an embodiment, a gap layer 220 is formed between the insulating layer 215 and the cover layer 225. A sample inlet 224 is provided in the gap layer corresponding to a part above the reaction reagent layer. The gap layer may be made of an adhesive material.

Any analyte that can be subject to electrochemical detection can be detected using the present invention. For example, the analyte may be glucose, lactate, urea, bicarbonate, 3-hydroxybutyric acid, (3-HBA), amino acid (such as L-glutamate, aspartate, L-lysine), hemoglobin, glutamic-pyruvic transaminase, ammonium, sodium, calcium, trace metal, and any other analyte which can be subject to electrochemical inspection.

The biosensor 100 can be used for detecting any liquid sample or liquidized sample. For instance, the detected samples include whole blood, serum, plasma, urea and saliva. Clinical samples, biologic samples, and environmental samples can be also detected, and these samples must be liquidized before being detected. The liquid sample may be a buffer liquid or suspension containing solid or gas biological substances.

In a specific embodiment, at least the inner surface of the cover layer 225 is made of a hydrophilic material. A vent hole 226 is provided in the cover layer, and then the reaction chamber of the sensor can be communicated with air outside. The vent hole may be a groove, but in other embodiments, the vent hole may be of any shape allowing air to circulate inside and outside the reaction chamber of the sensor. The vent hole may also be provided in the gap layer. In some embodiments, the cover layer may be be insulating ink printed on the sensor. The cover layer may further contain an adhesive, so that the cover layer can be adhered to a hydrophobic protection layer (if exists), the insulating layer 215, and the base plate.

Figure 9:
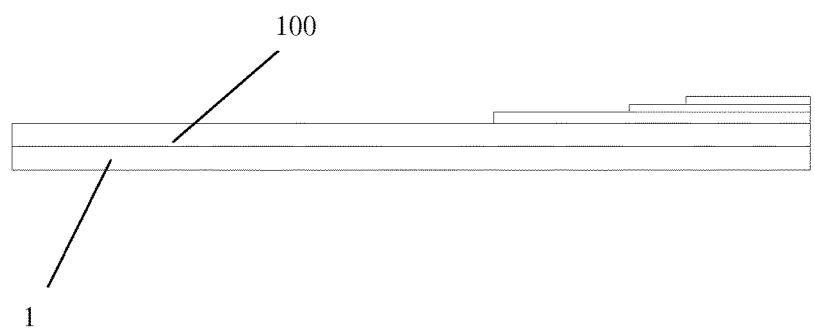
FIG. 9 is a schematic diagram of a first type of biosensor having the automatic encoding device.

As shown in FIG. 9, the automatic encoding device 1, and the working electrode and the counter electrode on the biosensor 100 are respectively positioned on two different insulating layers and are bonded together back to back.

Figure 10:
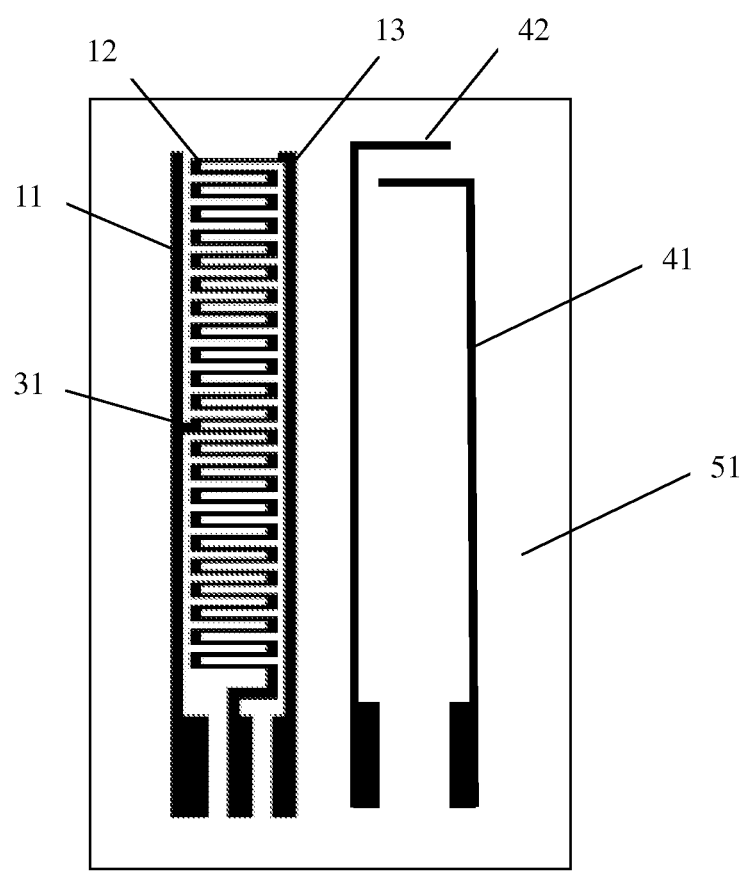
FIG. 10 is a schematic diagram of a second type of biosensor having the automatic encoding device.

As shown in FIG. 10, the automatic encoding device 1, and the working electrode and the counter electrode of the biosensor 100 are positioned on the same surface of the insulating layer 51. The biosensor includes the working electrode 41 and the counter electrode 42 for detecting the analyte, and the automatic encoding device includes a first electrode 11, a second electrode 12, and a third electrode 13.

Figure 11:
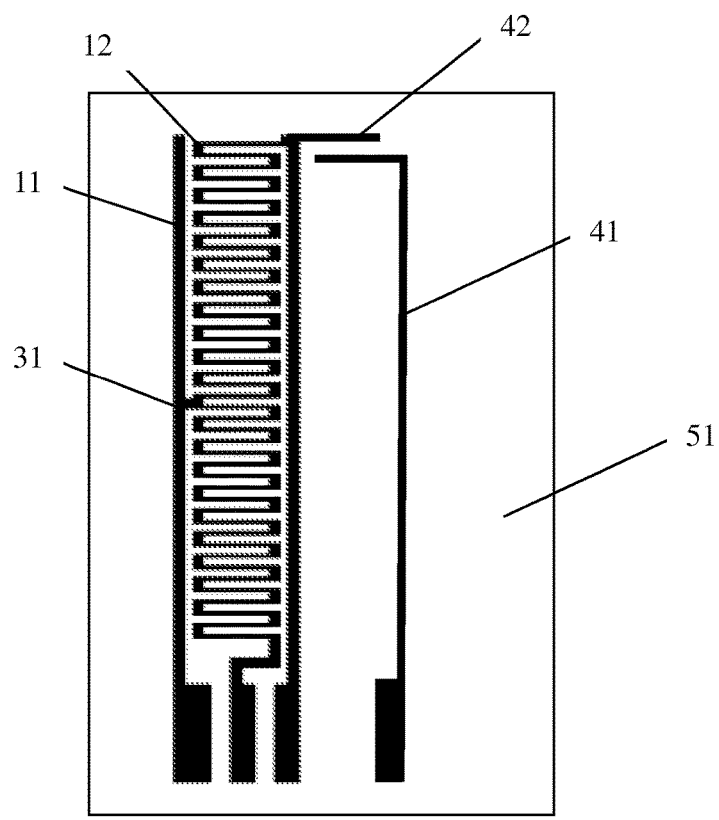
FIG. 11 is a schematic diagram of a third type of biosensor having the automatic encoding device.

As shown in FIG. 11, the automatic encoding device 1 is positioned on the same surface of the insulating layer 51 as the working electrode and the counter electrode of the biosensor 100. In this embodiment, the working electrode 41, the counter electrode 42, the first electrode 11, the second electrode 12, and the connecting point 31 for connecting the first electrode and the second electrode are disposed on the insulating layer. The automatic encoding device and the biosensor have a shared electrode 42. The second electrode 12 and the counter electrode 42 are connected to form a loop. In another embodiment, the second electrode 12 may form a loop selectively with the working electrode 41 or other reference electrodes. When the automatic encoding device on the biosensor is electrically connected with the detection instrument through the contacts, the detection instrument measures that the resistance of the loop 1 between the electrode 11 and the electrode 12 is R1, and the resistance of the loop 6 between the electrode 12 and the counter electrode 42 is R6. A resistance ratio S7 of the loop 1 to the loop 6 is obtained through equation 7.

$$S7 = K7 * \frac{R1}{R6} \quad (7)$$

where K7 is a correction coefficient.

The detection instrument selects corresponding technical parameters according to different values of S7, to finally obtain a detection result or determine the type of analyte detection performed.

The judgment method for distinguishing the biosensor and the automatic encoding device according to the present invention is not limited to the pattern structure listed above, but also includes various methods designed according to the principles of the present invention.

In the judgment method for distinguishing the biosensor and the automatic encoding device according to the present invention, the electric parameters of the loops are not limited to the resistances or the resistance ratios but also include current values and so on.

The electrodes and the connecting points may be made of materials with conductivity, such as carbon and silver, and may be manufactured on the insulating base plate by means of screen printing, electroplating, and so on. For example, the method for manufacturing the automatic encoding device by means of screen printing includes manufacturing a screen having a preset electrode shape, printing a conductive material onto an insulating base plate by using the screen and forming corresponding electrodes. The connecting points for connecting the electrodes may be disposed on the screen in advance and are printed on the insulating base plate at the same time when the electrodes are printed. The connecting points may be also loaded onto the electrode system by means of dotting or other methods after the electrode system is formed.

As the electrodes of the automatic encoding device are made of a conductive material, if the electrodes, particularly the snake-shaped units, are directly exposed outside, substances in the environment may be adhered to the electrodes, and then the actual resistances of the electrodes may be changed, causing the detection data to be inaccurate. Therefore, the electrodes of the automatic encoding device are covered with an isolating layer, and the isolating layer may be substances with weak conductivity, such as an adhesive sticker, a plastic piece, and UV curing ink.

The present invention further provides a manufacturing method for an automatic encoding device, and the manufacturing method includes the following steps:

providing an insulating base plate, where at least an electrode system including a first electrode 11, a second electrode 12, and a third electrode 13 is positioned on the insulating base plate;

connecting the first electrode with the second electrode through a first connecting point 31;

connecting the second electrode with the third electrode through a second connecting point 32; and determining a connection position of the first connecting point 31 between the first electrode and the second electrode according to information to be encoded by the automatic encoding device.

The connection position of the second connecting point 32 between the second electrode and the third electrode is determined according to the information to be encoded by the automatic encoding device.

Conducting materials are disposed at positions corresponding to the first connecting point and the second connecting point by means of printing. Multiple connection sites may also be formed between the first electrode and the second electrode by means of printing in advance, and subsequently other connection sites except the first connecting point between the first electrode and the second electrode are cut off by means of laser cutting. Multiple connection sites may also be formed between the second electrode and the third electrode by means of printing in advance, and subsequently other connection sites except the second connecting point between the second electrode and the third electrode are cut off by means of laser cutting.

In an embodiment, the second electrode 12 is composed of snake-shaped units.

In another embodiment, the insulating base plate is further provided with a fourth electrode 14, and the fourth electrode 14 is connected with the second electrode 12 through the third connecting point 32.

The automatic encoding devices described in the present invention are merely finite enumerations without departing from the spirit of the present invention, and other specific embodiments produced when persons skilled in the art combine the prior art with the present invention are not excluded.

What is claimed is:

1. A biosensor, comprising:
   an insulating base plate, and a working electrode (41) and a counter electrode (42) that are positioned on the insulating base plate, at least one of the working electrode (41) and the counter electrode (42) being provided with a reaction reagent layer,
   the biosensor further comprising an automatic encoding device, wherein the automatic encoding device comprises an electrode system positioned on the insulating base plate; the electrode system comprises a first electrode (11), a second electrode (12), and a third electrode (13); the first electrode (11), the second electrode (12), and the third electrode (13) respectively comprise a first contact (21), a second contact (22), and a third contact (23) which are electrically connected with a detection instrument; the first electrode (11) and the second electrode (12) are selectively electrically connected with a first connecting point (31); the second electrode (12) and the third electrode (13) are selectively electrically connected with a second connecting point (32), wherein (i) the location of the first connecting point (31) is configured and arranged to provide a loop formed by the first contact (21), the first connecting point (31), and the second contact (22) that encodes a predetermined electric parameter R1, (ii) the location of the second connecting point (32) is configured and arranged to provide a loop formed by the second contact (22), the second connecting point (32), and the third contact (23) that encodes a predetermined electric parameter R2, and (iii) the location of the first connecting point (31) and the second connecting point (32) are configured and arranged to provide a loop formed by the first contact (21), the first connecting point (31), the second connecting point (32), and the third contact (23) that encodes a predetermined electric parameter R3; and wherein values of predetermined electric parameters R1, R2, and R3 are selected to encode one or more parameters S1, S2, and S3 related to the identity or operation of the biosensor according to one or more of the following formulas:

$$S1 = K1 * \frac{R1}{R2}, \text{ or } S2 = K2 * \frac{R3}{R2}, \text{ or } S3 = K3 * \frac{R1}{R3}$$

wherein K1, K2, and K3 are correction coefficients, respectively.

2. The biosensor according to claim 1, wherein at least the second electrode comprises a zigzag snake-shaped structure, the second electrode comprises a plurality of snake-shaped units, and electric parameters of the snake shaped units are substantially the same.

3. The biosensor according to claim 2, wherein predetermined electric parameter R1 is defined according to the number of snake-shaped units comprised in the loop formed by the first contact (21), the first connecting point (31), and the second contact (22) and predetermined electric parameter R3 is defined the number of snake-shaped units comprised in the loop formed by the first contact (21), the first connecting point (31), the second connecting point (32), and the third contact (23).

4. The biosensor according to claim 1, further comprising a fourth electrode (14), wherein the fourth electrode (14) is electrically connected with the second electrode through a third connecting point (33), wherein the location of the third connecting point (33) is configured and arranged to provide a loop formed by a first contact (24), the third connecting point (33), and the second contact (22) that encodes a predetermined electric parameter R4.

5. The biosensor according to claim 1, further comprising a detection instrument configured and arranged to electrically connect to the first contact (21), the second contact (22), and the third contact (23) and to measure therefrom predetermined electric parameters R1, R2, and R3, to calculate one or more of S1, S2 and S3, and to use one or more of S1, S2 and S3 to control operation of the detection instrument.

* * * * *